United States Patent [19]

Lipscher

[11] Patent Number: 5,624,458
[45] Date of Patent: Apr. 29, 1997

[54] LANCET DEVICE

[75] Inventor: Ervin Lipscher, Budapest, Hungary

[73] Assignee: Anne Marie Varro, Mountain View, Calif.

[21] Appl. No.: 549,836

[22] PCT Filed: Oct. 19, 1994

[86] PCT No.: PCT/US94/11874

§ 371 Date: Oct. 18, 1995

§ 102(e) Date: Oct. 18, 1995

[87] PCT Pub. No.: WO95/10977

PCT Pub. Date: Apr. 27, 1995

[30] Foreign Application Priority Data

Oct. 20, 1993 [HU] Hungary ................................ 93 02966

[51] Int. Cl.$^6$ ........................................................ A61B 5/00
[52] U.S. Cl. ................................................ 606/181; 128/770
[58] Field of Search ................................ 606/181–185; 128/667, 770

[56] References Cited

U.S. PATENT DOCUMENTS

| | | | |
|---|---|---|---|
| 4,869,249 | 9/1989 | Crossman et al. | 606/182 |
| 5,026,388 | 6/1991 | Ingalz | 606/182 |
| 5,054,499 | 10/1991 | Swierczek | 606/182 |
| 5,201,324 | 4/1993 | Swierczek | 606/182 |
| 5,231,993 | 8/1993 | Haber et al. | 606/181 |
| 5,318,581 | 6/1994 | Sunmo | 606/181 |
| 5,402,798 | 4/1995 | Swierczek | 606/182 |

*Primary Examiner*—Michael Buiz
*Assistant Examiner*—William Lewis
*Attorney, Agent, or Firm*—Fish & Richardson P.C.

[57] ABSTRACT

A single-use lancet device is disclosed. The device comprises a housing with a compressible, flexible upper wall attached to the blunt end of a lancet, a lancet holder, and a perforable wall adjacent the tip of the lancet. Compressing the flexible upper wall drives the lancet tip through the perforable wall and into the body part. Spring tension developed in the flexible wall causes the lancet to retract into the housing after penetrating the body part. A stop mechanism then prevents repeated vertical movement of the lancet. The lancet is shielded before and after penetrating a finger or other body part.

12 Claims, 2 Drawing Sheets

LANCET DEVICE

BACKGROUND OF THE INVENTION

1. Field of the Invention

This invention generally relates to lancets and blood sampling devices.

2. Prior Art

In medical laboratories, doctors' offices, and the home, there is a frequent need to draw small amounts of blood for diagnostic purposes. Usually blood samples are drawn from the finger, earlobe or another easily accessible body part of the patient. Traditionally, this is done by cleaning the surface of the patient's finger and pricking it with a lancet. Drops of blood are collected in a tube or smeared on a microscope slide for further processing.

The medical personnel or others involved in taking the sample must assure the lancet needle penetrates to an appropriate depth, both to generate enough blood sample and to avoid excessive pain or an unnecessarily large wound. It is also important to keep the lancet from pricking the finger a second time to avoid uncontrolled sampling. Additional requirements are to avoid contaminating any surface of the lancet with blood, and to prevent infection of medical personnel by blood contact. In particular, since the discovery of human immunodeficiency virus (HIV or the AIDS virus), the need to avoid contact with blood samples and lancets has become acute.

Prior lancet devices have several drawbacks. Many lancets use springs to propel the lancet tip, or a needle, into the finger of the patient. These devices do not provide precise control over the depth of penetration of the lancet. Also, many prior lancet devices do not provide for automatic retraction of the lancet tip. Instead, the user must manually retract or cover the tip to prevent re-use. Further, most prior lancet devices require separate sterile packaging to prevent contamination of the lancet tip before it is used. Examples of prior devices having these disadvantages are found in U.S. Pat. Nos. 4,539,988, 4,624,253, and 5,074,872.

This invention avoids these drawbacks of the prior art and achieves the goals described above. The invention also helps prevent infection by blood-borne pathogens, such as the AIDS virus. The invention provides a blood sampling device which is reliable, hygienic, provides an optimum prick depth, and prevents re-use, while having low production costs.

SUMMARY OF THE INVENTION

A blood sampling system or lancet device comprises a piercing device in a closed housing. The housing comprises a perforable wall opposite the piercing device; the perforable wall is perforated by the piercing device at the moment of sampling. The piercing device is held in a cavity or recess on a platform formed integrally with a compressible, flexible upper wall of the device. This flexible upper wall of the housing permits vertical movement of the assembled piercing device; pressing on the flexible wall drives the piercing device through the perforable wall and into the patient's finger or other body part.

The flexible wall eliminates the need for a spring to retract the lancet. After sampling, the flexible wall itself retracts the lancet through spring tension developed in the material from which the wall is made.

The invention also includes means to control the depth of puncture by the piercing device. In one embodiment, the depth control means is a collar or rim integrally formed with the outside of the perforable wall of the housing. The collar defines a predetermined area; the center of the area is the piercing point at which the piercing device perforates the perforable wall. Pressure on the collar forces the skin to assume a tight, hemispherical shape, ensuring accurate puncture depth.

In one embodiment, the blood sampling device has a safety or stop mechanism which blocks repeated vertical movement of the piercing device by immobilizing the lancet inside the housing.

Other aspects of the invention are explained in the detailed description below and in the attached drawings.

DETAILED DESCRIPTION OF THE EMBODIMENTS

One embodiment of a blood sampling device or lancet device according to this invention is shown in FIG. 1–5. This embodiment is merely one example of the invention described and claimed herein. The figures should be considered exemplary and not limiting; the full scope of the invention is given in the appended claims.

Figure 1:
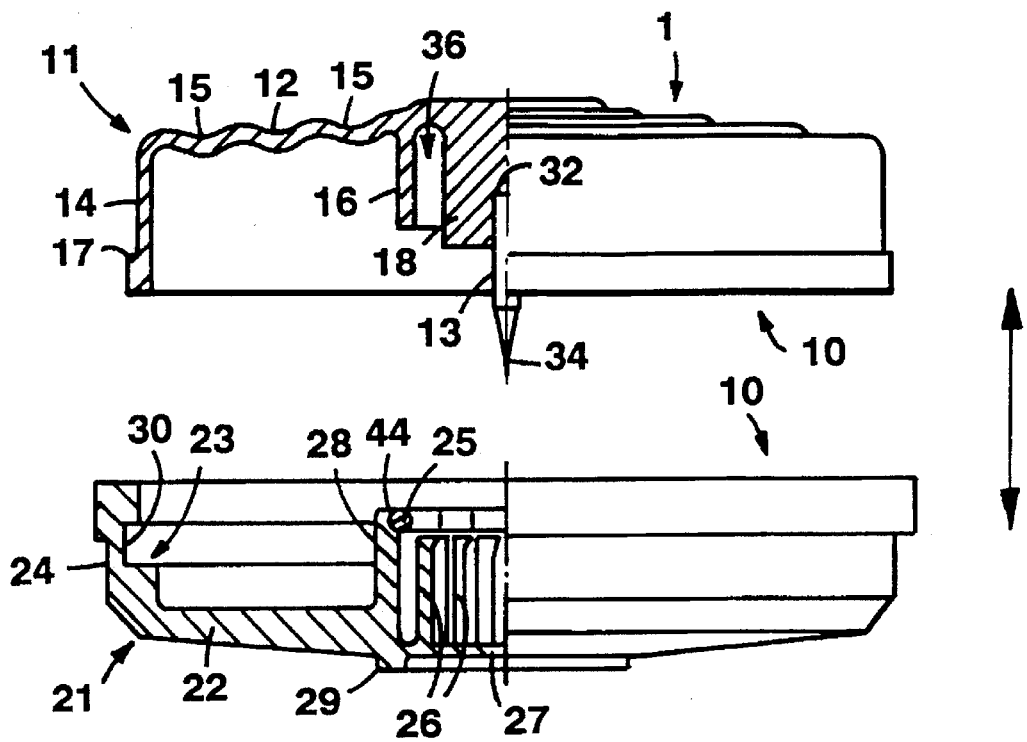
FIG. 1 is an exploded side elevation of one embodiment of a lancet device of the invention, shown in partial cross-section.

Referring first to FIG. 1, in one embodiment, the invention provides a lancet device 1 comprising an enclosed housing or body 10, preferably made of styrene plastic, polyethylene, polypropylene, other polymers, metals, alloys, or an equivalent resilient material. The housing 10 comprises an upper wall 11 and a lower wall 21. The upper wall 11 comprises a compressible wall portion 12 which is flexible; the upper wall 11 is surrounded by a circular rim 14. In one embodiment, the compressible wall portion 12 is made flexible by molding a plurality of concentric grooves 15 in the wall portion.

Figure 2:
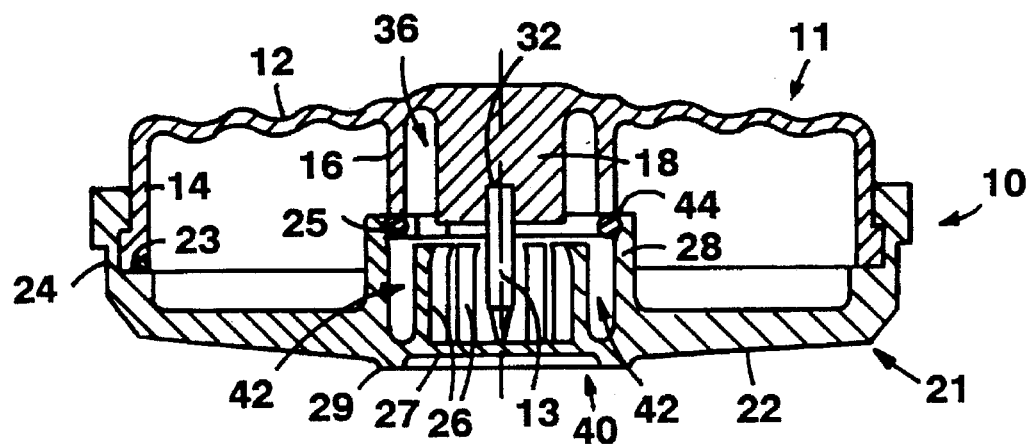
FIG. 2 is a section view of the embodiment of FIG. 1 shown before use.

The rim 14 of the upper wall 11 has an outwardly protruding shoulder 17 which snaps into a groove 30 in the perimeter 24 of the lower wall 21, as shown in FIG. 2.

The device further comprises a skin piercing device or lancet 13, tightly held in a lancet holder or recess 18 formed on the inside of the upper wall 11. The recess 18 can be a solid protrusion with a cylindrical cavity or an equivalent structure to tightly hold the blunt end 32 of the lancet 13 adjacent the upper wall 11, while the sharp end 34 of the lancet protrudes downward. The lancet can be cemented into the recess 18 or molded in place. The recess 18 is surrounded by a support rim 16, with a small gap 36 between the recess and the support rim. The function of the rim is described below.

The puncturing device 13 can comprise a lancet (i.e., a solid sharp-tipped pricking device), a needle, a sharpened sampling tube, a knife blade or scalpel, or any other perforating device adapted to pierce skin.

The lower part of the housing 21 includes a flat retaining wall 22 with a thin, centrally disposed perforable wall portion 27. The perforable wall can comprise thinly molded plastic, including the same plastic material used for the rest of the device. Alternatively, the perforable wall can comprise a thin metal film, a MYLAR layer, nylon sheet, or any other material which has high shear strength and relatively low tensile or perforation strength. The perforable wall portion is positioned perpendicular to and adjacent the sharp tip 34 of the lancet inside the upper housing, enabling the lancet to perforate the perforable wall 12 when the flexible wall is pushed down.

Figure 5:
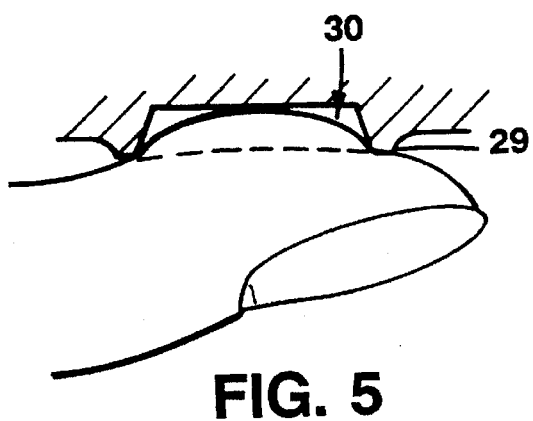
FIG. 5 is a side view of the embodiment of FIG. 1 shown during operation.

As shown in FIG. 2, a collar or rim 29 extends downward from the outer surface of the wall 22 of the lower housing 21. The collar 29 can be circular. When this collar 29 is pressed against a finger tip, as shown in FIG. 5, the collar 29 stretches the skin of the finger tip, forcing it to assume a tight curved or hemispherical surface 30. This forces the skin to move directly adjacent to the perforable wall, with no air gap or separation, so the lancet enters the skin immediately after perforating the wall 27. Thus, the collar 29 ensures that the piercing device 13 penetrates the fingertip to a predetermined and controlled depth. The collar 29 also ensures that the piercing device penetrates the skin in an optimally stretched state.

Referring again to FIG. 2, the lower part of the housing 22 further comprises a stop mechanism 40 for preventing the lancet from protruding through the perforable wall after perforating the perforable wall once. In one embodiment, the stop mechanism comprises a plurality of rods or columns 26 attached to the lower wall 22 and to the perforable wall 27, and projecting upwards towards the upper housing 11. The rods are positioned on the circumference of a circle defining perforable wall 27. The rods are relatively thin and can flex towards the center vertical axis of the housing.

The rod assembly 26 is surrounded by a support rim 28 with a small gap or channel 42 between the rod assembly 26 and the rim 28. The outer diameter of the support rim 16 on the upper housing is slightly smaller than the inner diameter of the support rim 28 around the rod assembly. In addition, the outside diameter of the lancet holder or recess 18 is smaller than the opening defined by the tips of the rod assembly 26.

A vertically movable ring 25 is positioned inside the support rim 28 level with the tips of rods 26. As shown in FIG. 2, the ring rests on inward facing shoulders 44 provided on the rim 28. The diameter of the ring 25 is approximately equal to the diameter of the support rim 16. The ring 25 on this shoulder is C-shaped (formed as an open, non-closed but nearly circular arc) so that it is compressible or expandable in diameter. The shoulders 44 provide a means for preventing the lancet from piercing the perforable wall, until sufficient downward force is applied to cause the ring to slip down off the shoulders and into gap 42.

Figure 3:
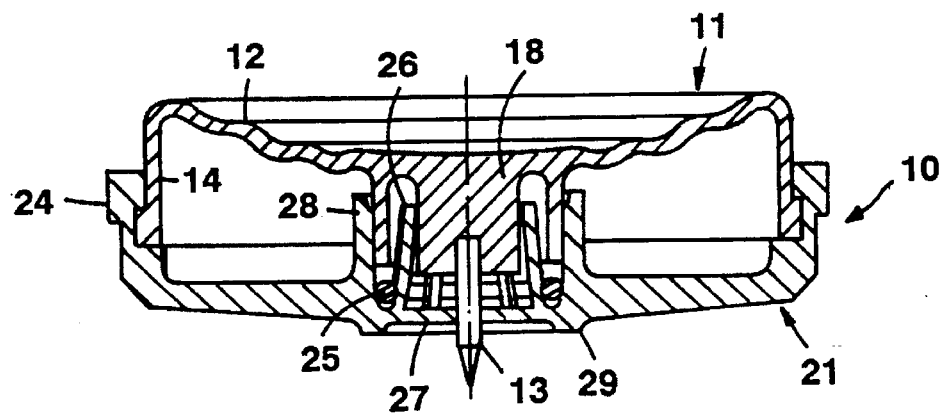
FIG. 3 is a section view the embodiment of FIG. 1 in use.
Figure 4:
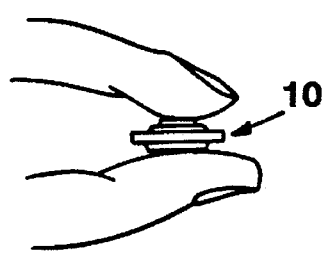
FIG. 4 is a side view of the lower portion of the embodiment of FIG. 1 positioned on a patient's finger.

The embodiment shown in the drawings operates as follows. As shown in FIG. 4, the device is positioned between two fingers and the upper wall 11 is pressed downward towards the target finger. As shown in FIG. 3, when the compressible wall 12 is pressed down, the support rim 16 and the lancet 13 move downwards and the rim 16 is driven into the gap 42 between the rim 28 and the rod assembly 26. Simultaneously, the tip of the lancet 13 is driven down through the perforable portion of the wall 27 and pierces an opening with a predetermined depth in the target finger or other body part.

During the piercing motion the rim 16 pushes the ring 25 down all the way into the gap 42 between the rim 28 and the rods 26. Because the width of the ring 25 is somewhat larger than the gap between the rim 28 and the rods 26, the ring 25 forces the rods to bend towards the center of the housing and towards the piercing device 13.

Once the pressure on the flexible wall 12 ceases, spring tension developed in the wall 12 causes the wall to return to its initial position, as shown in FIG. 2. Simultaneously, the recess 18 and the rim 16 slide out from the gap 42 between the rim 28 and the rods 26. The tip of the piercing device 13 moves with the recess 18 and retracts inside the capsule. When the recess 18 moves out of the gap between the rim 28 and the rods 26, the ring 25 stays in place and the tips of the rods 26 remain bent towards the vertical axis of the device due to pressure exerted by the ring 25. Thus, if the flexible wall is pressed a second time, the inward bent rods create a physical barrier blocking downward movement of the recess 18, stopping it at the bent tips of the rods and preventing the piercing device from reaching the perforable wall portion 27 of the lower housing a second time.

This stop mechanism ensures that the device can be used just once, and prevents accidental pricking by the piercing device. Use of a fully enclosed housing also assures that the used lancet is not accessible, which is crucial to prevent accidental injury or infection; thus, the device prevents both accidental or intentional multiple use. An important feature of the invention is that the piercing lancet 13 is not accessible at any time before or after the drawing of blood.

The depth of the skin penetration may be varied by changing the dimensions of various parts of the device. For example, changing the length of the rim 26 will change the penetration depth of the piercing device. This enables the device to be adapted for use with geriatric or pediatric individuals.

The usage described above with reference to FIG. 4 is only one of the potential uses of the invention. The exemplary use described above is advantageous when a patient, such as a diabetic, is performing blood sampling for self-monitoring purposes. The invention is also useful for medical personnel to perform blood sampling. In this procedure the patient's finger is held by the index finger of the medical personnel or is positioned on a horizontal surface. The person performing the blood sampling then positions the blood sampling device on top of the patient's finger and triggers the device with downward pressure. After the patient's finger is pricked, the device retracts the piercing lancet to its interior, excluding any potential for infections or contamination. The blood sample is then collected by pressing the pierced finger and collecting the blood into a tube or on a slide.

Another advantage of this device is single handed operation. As shown in FIG. 4, the device can be grasped, held and actuated by just two fingers of the same hand. This is easy and convenient for those doing home blood testing or monitoring.

The invention enables simple, accurate positioning and accurate piercing depth without special training or experience. These features assure that blood sampling with the device is fast and generates minimum discomfort.

Also, the invention causes a light finger prick, resulting in a small wound which ordinarily closes soon after the removal of the blood sampling device, without wasting or smearing blood, thus ensuring hygiene and avoiding the potential for infection.

The invention can be made of simple molded plastic parts at low cost; it is also simple to assemble and manufacture. The embodiment shown in FIGS. 1–5 can be manufactured by molding the upper and lower walls from a suitable material, placing a ring 25 in position, securing a lancet in the upper wall, and pressing the upper and lower walls together. This ease of manufacture is a significant advantage of this invention.

In one embodiment, the invention can be made in a disc like plastic or polymer housing, consisting of an upper and a lower portion. In this embodiment the invention can be made from injection-molded plastic with a diameter of 20 mm, height of 8 mm and a mass of about 2 g. The upper portion is compressible and flexible. Centered on the inner surface is a circular piercing device assembly platform, the lower perimeter of which is surrounded by a rim which is capable of exerting downward pressure. The lower portion includes a sealed perforable wall and contains on its inner surface a plurality of plastic rods, positioned concentrically in a circle. These rods project towards the upper body and are surrounded by a plastic support rim. A free moving flexible ring is located between the rods and the support rim, preferably positioned at the inner rim and level with the end of the rod assembly. The width of the flexing ring is equal or larger, than the gap between the rim and the rod assembly. The pressure rim, projecting downwards from the upper body is resting on the flexing ring.

In this embodiment, the plastic rod assembly is the blocking mechanism which safeguards against repeated use. After the device is triggered and the flexible wall has pulled the lancet back inside the housing, the flexing ring is forced into the gap between the supporting rim and the rod assembly. The flexing ring bends the individual rods inwards towards the perpendicular axis of the rod circumference. As a result of this action the upper portion of the rod assembly contracts, which in turn prevents repeated downward movement of the piercing lancet.

I claim:

1. A lancet device, comprising:
   a skin piercing device having a sharp tip and a blunt end;
   a closed housing around the piercing device, the housing having a perforable wall adjacent the tip, and a flexible wall adjacent to the blunt end opposite the perforable wall for driving the piercing device through the perforable wall; and
   a variable depth stop mechanism comprising at least one inwardly deformable column on the perforable wall, whereby downward pressure on the ring forces the column to deform inward, creating a physical barrier blocking downward movement of the piercing device and preventing the piercing device from reaching the perforable wall a second time.

2. The lancet device as recited in claim 1, further comprising an annular rim having a shoulder on which the ring rests until dislodged by sufficient downward pressure.

3. The lancet device as recited in claim 1, further comprising a rim on the perforable wall whereby pressure of the rim on a body part causes the piercing device to protrude through the perforable wall to a predetermined depth.

4. The lancet device as recited in claim 1, wherein the flexible wall comprises a rigid center portion surrounded by a plurality of grooves capable of flexing.

5. The lancet device as recited in claim 2, wherein the annular rim is disposed to act as a puncture depth stop for the piercing device.

6. A lancet device, comprising:
   a needle having a sharp tip and a blunt end secured in a needle holder;
   a closed housing surrounding the needle, comprising:
      a perforable face adjacent the tip of the needle;
      a flexible face opposite the perforable face adjacent the blunt end of the needle and attached to the needle holder; and
   a stop mechanism comprising at least one laterally flexible column on the perforable wall, and a detachable ring on the flexible wall, whereby downward pressure on the ring forces the column to deform inward, creating a physical barrier blocking downward movement of the piercing device and preventing the piercing device from reaching the perforable wall a second time.

7. The lancet device as recited in claim 6, further comprising a rim on the perforable wall whereby pressure of the rim on a body part causes the piercing device to protrude through the perforable wall to a predetermined depth.

8. The lancet device as recited in claim 6, further comprising an annular rim having a shoulder on which the ring rests until dislodged by sufficient downward pressure.

9. The lancet device as recited in claim 8, wherein the annular rim is disposed to act as a puncture depth stop for the piercing device.

10. The lancet device as recited in claim 6, wherein the flexible face comprises a rigid center portion surrounded by a plurality of grooves capable of flexing.

11. A blood sampling device for fingerpricking comprising a piercing lancet enclosed in a housing comprising a puncturable wall portion opposite the piercing lancet, the piercing lancet being fixed in a cylindrical cavity;
    a compressible wall opposite the puncturable wall which allows the piercing lancet to move towards the puncturable wall portion; and
    a rim on the outer surface of the housing centered around a target puncture point of the lancet on the puncturable wall portion, whereby pressure of the rim on a body part causes the lancet to protrude through the puncturable wall to a predetermined depth; and
    a variable depth stop mechanism having at least one inwardly deformable column on the puncturable wall and a detachable ring on the compressible wall, whereby downward pressure on the ring forces the column to deform inward creating a physical barrier blocking downward movement of the piercing device and preventing the piercing device form reaching the perforable wall a second time.

12. The blood sampling device as recited in claim 11, further comprising an annular ring having a shoulder on which the ring rests until dislodged by sufficient downward pressure.

* * * * *